United States Patent
Koch

(10) Patent No.: US 6,929,611 B2
(45) Date of Patent: Aug. 16, 2005

(54) DEVICE FOR MEASURING THE BODY TEMPERATURE

(75) Inventor: Jochim Koch, Ratzeburg (DE)

(73) Assignee: Dräger Medical AG & Co. KGaA, Lübeck (DE)

( * ) Notice: Subject to any disclaimer, the term of this patent is extended or adjusted under 35 U.S.C. 154(b) by 369 days.

(21) Appl. No.: 10/171,050

(22) Filed: Jun. 13, 2002

(65) Prior Publication Data

US 2003/0032893 A1 Feb. 13, 2003

(30) Foreign Application Priority Data

Aug. 11, 2001 (DE) .......................................... 101 39 705

(51) Int. Cl.$^7$ ................................................. A61B 5/00
(52) U.S. Cl. ..................................................... 600/549
(58) Field of Search ........................ 600/549; 128/903; 340/586, 573.1; 2/5

(56) References Cited

U.S. PATENT DOCUMENTS

| | | | |
|---|---|---|---|
| 4,279,037 A | 7/1981 | Morgan | |
| 5,200,736 A | * 4/1993 | Coombs et al. | 340/586 |
| 6,547,745 B1 | * 4/2003 | Rubinstein | 600/549 |
| 2001/0044588 A1 | * 11/2001 | Mault | 600/549 |

FOREIGN PATENT DOCUMENTS

| | | |
|---|---|---|
| DE | 23 27 374 | 12/1974 |
| DE | 198 00 753 | 7/1999 |
| DE | 100 38 247 A1 | 5/2001 |
| EP | 0 815 754 A1 | 7/1998 |

* cited by examiner

Primary Examiner—Max F. Hindenburg
Assistant Examiner—Brian Szmal
(74) Attorney, Agent, or Firm—McGlew and Tuttle, P.C.

(57) ABSTRACT

A device method and system are provided for measuring the body temperature in the area of the head. Reliable measured values are furnished even during movement and physical exercise. The device includes a head strap (1), whose strap elements (2, 3) are in contact at least partially as strap sections (7, 10) with the scalp of a user (4) of the headband and in which at least one of the strap sections (7) is designed for receiving a first temperature sensor (12) measuring the skin temperature.

17 Claims, 3 Drawing Sheets

DEVICE FOR MEASURING THE BODY TEMPERATURE

FIELD OF THE INVENTION

The present invention pertains to a device for measuring the body temperature with a head strap.

BACKGROUND OF THE INVENTION

A large number of head straps, with which protective helmets, hoods or masks can be fastened to the head of the user of the respirator, have become known among respirator products. A head strap, which comprises individual strap elements, which can be adapted to the shape of the head of the user of the head strap, has become known from U.S. Pat. No. 4,279,037. Such head straps can be used by a large number of persons who need head protection. On the one hand, the head strap shall be able to be fastened nondisplaceably on the head of the user of the head strap, but, on the other hand, it shall be able to be easily removed. In persons who perform physical exercise and wear a head strap, there is increasingly a need for detecting and monitoring physical data in order to recognize physical overexertion in time. The body temperature is a physiological parameter from which the general condition can be deduced. Even though it has been known from medical treatment devices for infants that the skin temperature can be detected in the area of the abdomen by means of a temperature sensor placed there, these measurements are carried out only on subjects who are not moving or are moving only slightly. The temperature sensor is therefore fastened to the skin at this location with an adhesive strip only.

SUMMARY OF THE INVENTION

The basic object of the present invention is to provide a device for measuring the temperature in the area of the head, which also furnishes reliable measured values during movement and physical exercise.

According to the invention, a device for measuring the body temperature is provided including a head strap. The head strap has strap elements in contact with the scalp of a headband user at least partially as strap sections. At least one of the strap sections is designed for receiving a first temperature sensor measuring the skin temperature.

The advantage of the present invention is essentially that by placing a first temperature sensor on a strap section of the head strap, which is directly in contact with the scalp of the user of the head strap, measurement of the body temperature is possible on a predetermined area on the head immediately after putting on the head strap. A nonmovable fixation of the first temperature sensor on the head is also achieved by means of the head strap during physical exercise, because it is firmly in contact there and can be fixed in a defined preferred position only. The head strap may comprise individual strap sections with, e.g., a forehead band and a headband, which can be individually adapted to the shape of the headband user's head. However, it is also possible to provide an elastic body in the form of a stocking as a head strap, which is pulled over the head. The first temperature sensor is fastened to the head strap such that it is directly in contact with the scalp.

The first temperature sensor is advantageously arranged on the forehead of the user of the headband. A forehead band is provided for this purpose as a band element, on which the first temperature sensor is arranged such that it lies directly on the skin and is pressed onto the skin by the internal stress of the forehead band. The band section at which the first temperature sensor is located is advantageously positioned such that it is in contact with the forehead and the lateral blood vessels of the temple and somewhat below the hairline over a vertical axis of the center of the eye between the central blood vessels. A measuring point in this area is especially suitable for measuring the headband user's core temperature.

As an alternative, the first temperature sensor may also be fastened with a headband as a band element on the headplate, preferably in the area where the fontanelle is located in infants. This measuring point is not surrounded by large blood vessels that could affect the temperature measurement.

A second temperature sensor, which measures the temperature close in space in the environment of the head strap, is advantageously provided. The temperature of the close in space or interior space is measured with the second temperature sensor. This makes it possible to calculate the body core temperature from the formula A: $tc = th1 + (th1 - th2) * Ks/Kg$, in which
tc=core temperature,
th1=temperature near the skin,
th2=temperature close in space,
Ks=coefficient of thermal conductivity for the sensor,
Kg=coefficient of thermal conductivity for the tissue.

The coefficient of thermal conductivity Ks of the sensor is determined by the insulation between the first and second temperature sensors. For example, a value of about 40 $W/m^2*K$ is obtained in case of a foam type insulation of about 2 mm. The coefficient of thermal conductivity Kg of the tissue can be determined empirically. Values between 40 $W/m^2*K$ and 52 $W/m^2*K$ are known from clinical studies. It varies with the position in space.

The fixation of the strap section accommodating the first temperature sensor is improved when the strap section is designed at least partially as a pressure-sensitive element.

The head strap is advantageously designed as the inner part of a protective helmet with a fixed outer shell, wherein the inner part is in contact with the head of the user of the protective helmet. The inner part may comprise discrete straps and is designed as a foamed inner shell.

If the temperature measurement is carried out with two temperature sensors, the first temperature sensor is used to detect the temperature near the skin, and the second temperature sensor is positioned such that the temperature in the space between the inner part and the inner wall of the outer shell of the protective helmet can be measured with it. The body core temperature of the protective helmet's user is determined from the two temperatures according to the calculation formula A.

The first temperature sensor and the second temperature sensor are advantageously integrated into a double temperature sensor in such a way that the temperature sensors are arranged in a sensor housing on two opposite housing parts, which are arranged at spaced locations from one another in a thermally isolated manner. In the double temperature sensor, one of the temperature sensors is directly on the skin, while the other temperature sensor arranged opposite measures the temperature of the environment.

The temperature sensors are advantageously connected to an evaluating circuit for transmitting measured temperature values to a receiving station. The evaluating circuit is located directly in the vicinity of the temperature sensors in order to amplify the measured signals and to process possible calibration and correction values. The receiving station is located, by contrast, in the area of sight of the user of the headband or helmet in order to display the measured temperature. If the user of the headband or helmet is also carrying a respirator with him, the receiving station may be integrated in the respirator and additionally also assume measuring and monitoring tasks for the respirator. Such measuring and monitoring tasks are, e.g., the measurement of the pressure in the cylinder in order to make it possible to calculate the remaining operating time, the monitoring of the movement of the user of the respirator with a motion sensor, and the measurement of the ambient temperature.

It is especially advantageous to provide a wireless transmission section between the evaluating circuit and the receiving station. It is possible as a result to remove or put on the head strap or the protective helmet with integrated temperature sensor without a cable connection having to be disconnected or established.

A contact switch, which is activated when the head strap is put on and switches on the power supply for the evaluating circuit, is advantageously provided on the head strap. The contact switch is preferably actuated by pressure when the head strap is placed on the user's scalp and the contact switch is activated as a result by contact.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

DESCRIPTION OF THE PREFERRED EMBODIMENT

Figure 1:
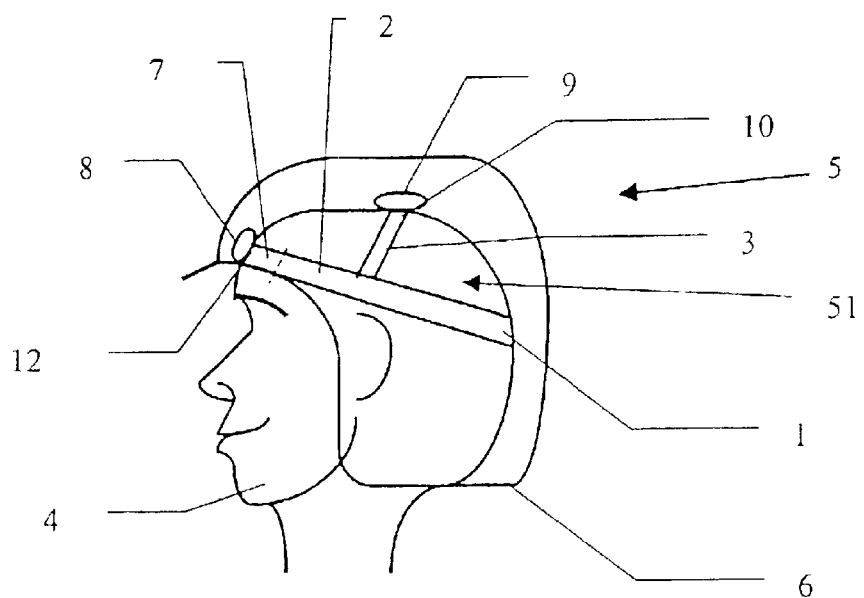
FIG. 1 is a schematic view of a head strap with a temperature sensor in a protective helmet.

Referring to the drawings in particular, FIG. 1 schematically shows a head strap 1 with a forehead band 2 and a headband 3, which lies on the head of a headband user 4 and is an inner part 51 of a protective helmet 5 with fixed outer shell 6. A double temperature sensor 8 is fastened to a strap section 7. The reference number 9 at the strap section 10 of the headband 3 indicates an alternative position for the double temperature sensor 8.

Figure 2:
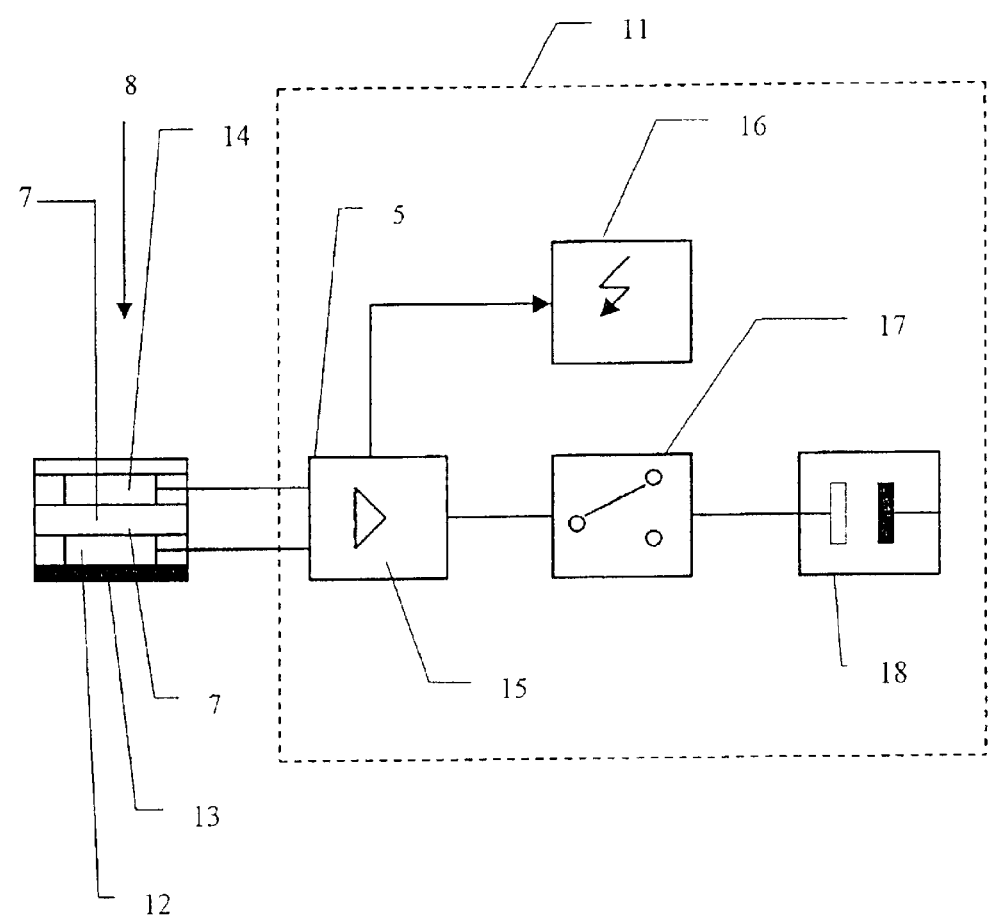
FIG. 2 is a schematic view showing the temperature sensor connected to an evaluating circuit.

FIG. 2 illustrates the design of the double temperature sensor 8 and of an evaluating circuit 11, to which the double temperature sensor 8 is connected.

The double temperature sensor 8 comprises a first temperature sensor 12, which is in contact with the scalp 13 of the headband user 4, and a second temperature sensor 14, which is arranged opposite the first temperature sensor 14 in a thermally insulated manner. The double temperature sensor 8 is fixed on the scalp 13 by the strap section 7 as part of the forehead band 2.

An evaluating circuit 11 contains an amplifier 15 with computing unit, a first transceiver-receiver 16 and a contact switch 17, via which the amplifier 15 is connected to a battery 18. The contact switch 17 is arranged on the strap section 7 and is actuated by pressure when the head strap 1, FIG. 1, is put on. As a result, the amplifier 15 and the transceiver-receiver 16 are switched on automatically when the head strap 1 is put on.

Figure 3:
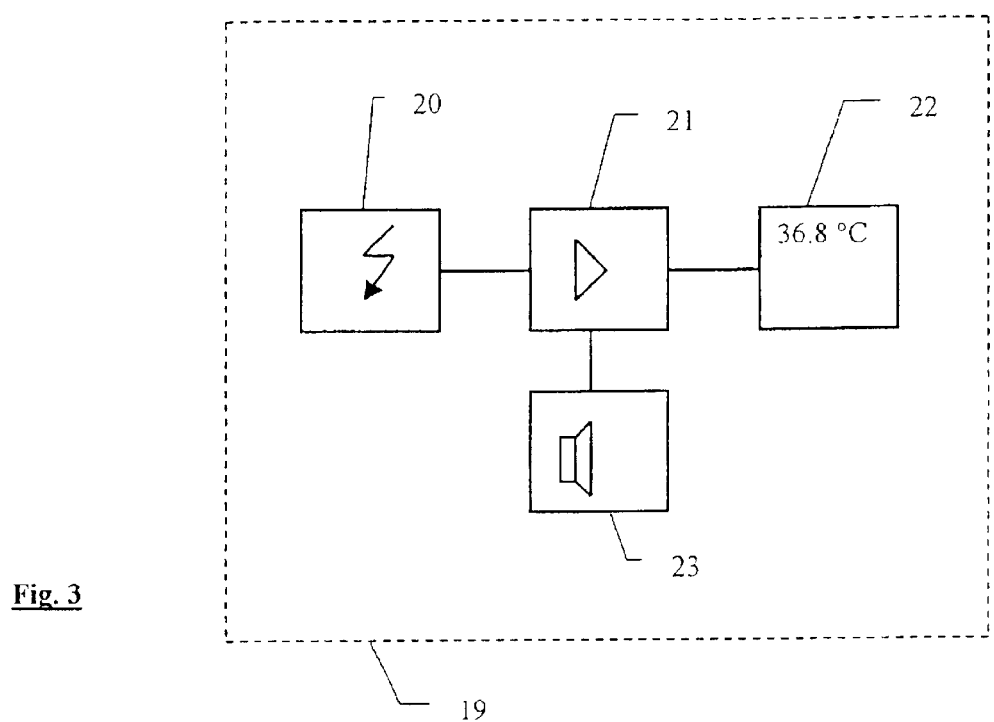
FIG. 3 is a schematic view showing a receiving station for the measured temperature values received.

A receiving station 19 shown in FIG. 3 comprises a second transceiver-receiver 20, an evaluating circuit 21 with a display unit 22, and an alarm means 23. The receiving station 19 is located either on the body of the headband user 4, so that the user can read the measured temperature directly, or it is accommodated in a central monitoring station at some distance.

The device according to the present invention operates as follows: The temperature of the scalp 13 is measured with the first temperature sensor 12, while the second temperature sensor 14 detects the temperature close in space or interior space between the head strap 1 and the inner surface of the outer shell 6 of the protective helmet. Both measured values are standardized in the amplifier 15 and transmitted to the evaluating electronic unit 21 in the receiving station 19 via the first transceiver-receiver 16. The body core temperature of the headband user 4 is calculated in the evaluating electronic unit 21 from the values measured with the temperature sensors 12, 14 according to the calculation formula $$tc = th1 + (th1 - th2) * Ks/Kg$$

and displayed on the display unit 22. When the actual value exceeds or drops below limit values set previously, the alarm 23 is activated. If the data are passed on to a central monitoring station, the mission leader, care giver or trainer can decide there which persons must possibly be called back from the action.

While specific embodiments of the invention have been shown and described in detail to illustrate the application of the principles of the invention, it will be understood that the invention may be embodied otherwise without departing from such principles.

What is claimed is:

1. A device for measuring a body temperature of a subject, the device comprising:

a head positioning element with a section positioned adjacent to the scalp of a subject or adjacent to the fontanelle of the subject; and a double temperature sensor with a first temperature sensor and a second temperature sensor arranged as an assembly unit opposite each other, wherein said double temperature sensor is positioned by said head positioning element such that said first temperature sensor measures a temperature $th_1$ near the skin on the forehead of the said subject substantially in the middle between the eyes or on the head in the area of the fontanelle and said second temperature sensor measures a temperature $th_2$ close in space to the head or the forehead; and a body temperature evaluating unit determining the body temperature of the subject from the calculation formula $$tc = th_1 + (th_1 - th_2) * Ks/Kg$$

in which

Ks=coefficient of thermal conduction for the sensor and

Kg=coefficient of thermal conduction for the tissue.

2. A device in accordance with claim 1, wherein said head positioning element includes a strap holding said first temperature sensor fastened in an area of the forehead of the subject or in the area of the top side of the head of the subject, said strap accommodating said double temperature sensor and said double temperature sensor including an element that is at least partially self-sticking.

3. A device in accordance with claim 2, wherein said bead positioning element strap as a head strap.

4. A device in accordance with claim 3, wherein said head strap has strap elements at least partially in contact as strap sections with the scalp of the subject.

5. A device in accordance with claim 1, wherein said head positioning element includes strap sections as elements of an inner part of a protective helmet with a hard outer shell.

6. A device in accordance with claim 2, wherein said head positioning element includes strap sections as elements of a protective helmet wherein said strap sections are elements of an inner part of a protective helmet with a fix outer shell.

7. A device in accordance with claim 6, wherein said inner art is a helmet inner shell.

8. A device in accordance with claim 4, wherein said strap elements are elements of an inner part of a protective helmet with a fixed outer shell wherein said second temperature sensor is fastened in an area between the inner part an inner wall of the outer shell.

9. A device in accordance with claim 4, wherein said first temperature sensor and said second temperature sensor are arranged thermally insulated from one another.

10. A device in accordance with claim 4, further comprising a receiving station, wherein said first temperature sensor and said second temperature sensor are connected to said evaluating unit for transmitting measured temperature values to said receiving station.

11. A device in accordance with claim 10, further comprising a wireless transmission section provided between the evaluating unit and the receiving station.

12. A device in accordance with claim 10, further comprising a contact switch actuating at least said evaluating unit by which said evaluating unit can be brought into an operating position when the head strap is put on.

13. A method of monitoring a subject's body temperature, the method comprising:
providing a doable temperature sensor with a first temperature sensor and a second temperature sensor arranged as an assembly unit opposite one another;
positioning the first temperature sensor for measuring with said first temperature sensor the temperature $th_1$ near the skin on the forehead of the subject in the middle or on the head in the area of the fontanelle;
measuring with said second temperature sensor the temperature in the near environment;
and using the measured temperature near the skin and temperature in the near environment to determine the body core temperature of the subject from the calculation formula $$tc=th_1+(th_1-th_2) * Ks/Kg$$

in which
Ks=coefficient of thermal conduction for the sensor and
Kg=coefficient of thermal conduction for the tissue.

14. A body temperature measurement system, comprising:
a head strap with a strap section at least partially in contact with the scalp of a subject;
a first temperature sensor for measuring the skin temperature, said strap section supporting said first temperature sensor in contact with the scalp of a subject;
a helmet connected to said head strap;
a second temperature sensor connected to one or more of said first temperature sensor and said head strap, said first temperature sensor and said second temperature sensor being disposed in said helmet;
an evaluating circuit and a receiving station, wherein said first temperature sensor and said second temperature sensor are connected to said evaluating circuit for transmitting measured temperature values to said receiving station, said first temperature sensor measuring the temperature $th_1$ near of skin of the subject, wherein said first temperature sensor is fastened in an area of the forehead of the subject and said first temperature sensor and said second temperature sensor form a double sensor arrangement with said second temperature sensor measuring the temperature $th_2$ in the near environment within the helmet; and a body temperature evaluating unit determining the body temperature of the subject from the calculation formula $tc=th_1+(th_1-th_2) * Ks/Kg$ in which Ks=coefficient of thermal conduction for the sensor and Kg=coefficient of thermal conduction for the tissue; and a wireless transmission section provided between the evaluating unit and the receiving station.

15. A body temperature measurement system, comprising:
a head strap with a strap section at least partially in contact with the scalp of a subject;
a first temperature sensor for measuring the skin temperature $th_1$, said strap section supporting said first temperature sensor in contact with the scalp of a subject;
a helmet connected to said head strap;
a second temperature sensor connected to one or more of said first temperature sensor and said head strap for measuring a temperature $th_2$ close in space to the head a forehead, said first temperature sensor and said second temperature sensor being disposed in said helmet; and an evaluating circuit and a receiving station, wherein said first temperature sensor and said second temperature sensor are connected to said evaluating circuit for transmitting measured temperature values to said receiving station, said first temperature sensor measuring the temperature near of skin of the subject, wherein the strap section receiving said first temperature sensor is at least partially provided as a pressure-sensitive self sticking element;

a body temperature evaluating unit determining the body temperature of the subject from the calculation formula $tc=th_1+(th_{1-th2}) * Ks/Kg$ in which Ks=coefficient of thermal conduction for the sensor and Kg=coefficient of thermal conduction for the tissue; and a wireless transmission section provided between the evaluating unit and the receiving station.

16. A body temperature measurement system, comprising:
a head strap with a strap section at least partially in contact with the scalp of a subject;
a first temperature sensor for measuring the skin temperature $th_1$, said strap section supporting said first temperature sensor in contact with the scalp of a subject;
a helmet connected to said head strap;
a second temperature sensor connected to one or mare of said first temperature sensor and said head strap for measuring a temperature $th_2$ close in space to the head or forehead said first temperature sensor and said second temperature sensor being disposed in said helmet;

an evaluating circuit and a receiving station, wherein said first temperature sensor and said second temperature sensor are connected to said evaluating circuit for transmitting measured temperature values to said receiving station, said first temperature sensor measuring the temperature near of skin of the subject, wherein said strap section is an element of an inner shell part of said helmet with a fixed outer shell wherein said second temperature sensor is fastened in the area between the inner part and the inner wall of the outer shell; and a body temperature evaluating unit determining the body temperature of the subject from the calculation formula tc=$th_1$+($th_1$-$th_2$) * Ks/Kg in which Ks=coefficient of thermal conduction for the sensor and Kg=coefficient of thermal conduction for the tissue; and a wireless transmission section provided between the evaluating unit and the receiving station.

17. A body temperature measurement system, comprising:

a head strap with a strap section at least partially in contact with the scalp of a subject;

a first temperature sensor for measuring the skin temperature $th_1$, said strap section supporting said first temperature sensor in contact with the scalp of a subject;

a helmet connected to said head strap;

a second temperature sensor connected to one or more of said first temperature sensor and said head strap for measuring a temperature $th_2$ close in space to the head or forehead said first temperature sensor and said second temperature sensor being disposed in said helmet;

an evaluating circuit and a receiving station, wherein said first temperature sensor and said second temperature sensor are connected to said evaluating circuit to transmitting measured temperature values to said receiving station, said first temperature senor measuring the temperature near of skin of the subject, wherein said first temperature sensor and said second temperature sensor are integrated in one assembly unit providing a double temperature sensor, in which the temperature sensors are arranged opposite and thermally insulated from one another; and a body temperature evaluating unit determining the body temperature of the subject from the calculation formula tc=$th_1$=($th_1$-$th_2$) * Ks/Kg in which Ks=coefficient of thermal conduction for the sensor and Kg=coefficient of thermal conduction for the tissue; and a wireless transmission section provided between the evaluating unit and the receiving station.

* * * * *